US012658307B2

(12) United States Patent
Her et al.

(10) Patent No.: US 12,658,307 B2
(45) Date of Patent: Jun. 16, 2026

(54) LABELING METHOD AND COMPUTING DEVICE BY DETECTING LESION REGION IN IMAGES USING A LEARNED NETWORK FUNCTION

(71) Applicant: DDH INC., Seoul (KR)

(72) Inventors: Soo Bok Her, Seoul (KR); Hak Kyun Shin, Seoul (KR); Dong Yub Ko, Seoul (KR)

(73) Assignee: DDH INC., Seoul (KR)

( * ) Notice: Subject to any disclaimer, the term of this patent is extended or adjusted under 35 U.S.C. 154(b) by 310 days.

(21) Appl. No.: 18/269,931

(22) PCT Filed: May 12, 2021

(86) PCT No.: PCT/KR2021/005921
§ 371 (c)(1),
(2) Date: Jun. 27, 2023

(87) PCT Pub. No.: WO2022/177069
PCT Pub. Date: Aug. 25, 2022

(65) Prior Publication Data
US 2024/0055103 A1      Feb. 15, 2024

(30) Foreign Application Priority Data

Feb. 16, 2021    (KR) ........................ 10-2021-0020398

(51) Int. Cl.
*G16H 30/40* (2018.01)
*G06T 3/40* (2024.01)
(Continued)

(52) U.S. Cl.
CPC .............. *G16H 30/40* (2018.01); *G06T 3/40* (2013.01); *G06T 3/4053* (2013.01);
(Continued)

(58) Field of Classification Search
CPC ......... G06T 2207/20081; G06T 3/4061; G06T 7/0012; G06T 2207/30096; G06T 7/11;
(Continued)

(56) References Cited

U.S. PATENT DOCUMENTS 10,290,101 B1 * 5/2019 Podilchuk ............... G06T 11/00
2007/0127796 A1 * 6/2007 Nay ........................ G06V 10/46
382/128

(Continued)

FOREIGN PATENT DOCUMENTS

CN       110570353 A  * 12/2019 ............... G06N 3/08
KR  10-2019-0103937 A     9/2019
(Continued)

OTHER PUBLICATIONS

Long, Xingyu. (2020). Keras documentation: Image Super-Resolution using an Efficient Sub-Pixel CNN. Keras.io. https://keras.io/examples/vision/super_resolution_sub_pixel/ (Year: 2020).*
(Continued)

*Primary Examiner* — Sumati Lefkowitz
*Assistant Examiner* — Ryan P Potts
(74) *Attorney, Agent, or Firm* — Bridgeway IP Law Group, PLLC; Sang Ho Lee; Hyun Woo Shin

(57)                ABSTRACT

A labeling method and a computing device by detecting lesion region in images using a learned network function. The method includes obtaining a medical image, detecting and displaying a region of interest corresponding to at least one subject disease through a learned network function, and labeling a lesion region corresponding to the at least one subject disease on the medical image according to the region of interest and user inputs. The labeling includes receiving a first user input for choosing a selected region within the region of interest, setting a reference pixel value based on the selected region, detecting and displaying a lesion esti-
(Continued)

mation region having pixel values within a predetermined range from the reference pixel value, and correcting the lesion estimation region according to a second user input to label the lesion region.

18 Claims, 8 Drawing Sheets

(51) Int. Cl.

| | |
|---|---|
| *G06T 3/4053* | (2024.01) |
| *G06T 7/00* | (2017.01) |
| *G06T 7/11* | (2017.01) |
| *G06T 7/187* | (2017.01) |
| *G16H 50/20* | (2018.01) |

(52) U.S. Cl.
CPC ............. *G06T 7/0012* (2013.01); *G06T 7/11* (2017.01); *G06T 7/187* (2017.01); *G16H 50/20* (2018.01); *G06T 2207/20081* (2013.01); *G06T 2207/20084* (2013.01); *G06T 2207/20104* (2013.01); *G06T 2207/20132* (2013.01); *G06T 2207/30096* (2013.01); *G06T 2210/41* (2013.01)

(58) Field of Classification Search
CPC . G06T 2207/20132; G06T 2207/20104; G06T 3/4053; G06T 3/40; G06T 2207/20084; G06T 7/187; G06T 2210/41; G16H 30/40; G16H 50/20
See application file for complete search history.

(56) References Cited

U.S. PATENT DOCUMENTS

| | | | | |
|---|---|---|---|---|
| 2014/0146076 A1* | 5/2014 | Kim | ...................... | G06T 11/60 |
| | | | | 345/619 |
| 2015/0160843 A1* | 6/2015 | Kim | .................... | G06F 3/0488 |
| | | | | 715/764 |
| 2018/0114086 A1 | 4/2018 | Lee et al. | | |
| 2019/0392267 A1* | 12/2019 | Tang | ................... | G06V 30/194 |
| 2019/0392943 A1 | 12/2019 | Sorenson et al. | | |
| 2020/0364852 A1* | 11/2020 | Park | ..................... | G06T 7/0012 |
| 2022/0139531 A1* | 5/2022 | Wang | .................... | G16H 50/20 |
| | | | | 382/128 |

FOREIGN PATENT DOCUMENTS

| | | |
|---|---|---|
| KR | 10-2020-0017607 A | 2/2020 |
| KR | 10-2102255 B1 | 4/2020 |
| KR | 10-2020-0131737 A | 11/2020 |

OTHER PUBLICATIONS

C. Pavlopoulou, A. Kak and C. Brodley, "An interactive framework for boundary delineation for medical CBIR," Proceedings IEEE Workshop on Content-Based Access of Image and Video Libraries (CBAIVL 2001), Kauai, HI, USA, 2001, pp. 9-16, doi: 10.1109/IVL.2001.990850. (Year: 2001).*

* cited by examiner

21

<u>800</u>

LABELING METHOD AND COMPUTING DEVICE BY DETECTING LESION REGION IN IMAGES USING A LEARNED NETWORK FUNCTION

TECHNICAL FIELD

The present invention relates to a labeling method and a device therefor.

BACKGROUND ART

Recently, interests and demands for artificial intelligence have increased. Also, studies in the field of artificial intelligence have been developed. To perform supervised learning of an artificial neural network, above all, it is necessary to produce learning data. To produce the learning data, further, labeling for the learning data has to be performed. A large quantity of learning data is needed to enhance the accuracy of artificial intelligence, and if the labeling for the production of learning data is performed directly by a person, the time needed for the labeling increases exponentially.

Therefore, there is a definite need for a new method capable of decreasing the time and endeavor required for the labeling for learning data production.

DISCLOSURE

Technical Problem

Accordingly, it is an object of the present invention to provide a labeling method and a computing device therefor that are capable of labeling a lesion region on a medical image.

The technical problems of the multi-modality medical image analysis method and apparatus to be achieved through the present invention are not limited as mentioned above, and other technical problems not mentioned herein will be obviously understood by one of ordinary skill in the art through the following description.

Technical Solution

According to an aspect of the present invention, a labeling method is provided. The labeling method may include the steps of acquiring a medical image, receiving the medical image, detecting regions of interest corresponding to at least one subject disease through a learned network function, and displaying the regions of interest on the medical image, and labeling a lesion region corresponding to the subject disease on the medical image according to the regions of interest and user inputs to the regions of interest.

The labeling method may further include the step of setting the subject disease according to a user input.

The labeling method may further include the step of correcting at least one of the regions of interest according to a user input and cropping and storing the corrected region of interest from the medical image.

Further, the step of labeling the lesion region corresponding to the subject disease may include the steps of: receiving a first user input for selecting a given region in the region of interest, setting a reference pixel value for the selected given region, detecting a region within the range of given pixel values from the reference pixel value as a lesion estimation region and displaying the detected lesion estimation region on the region of interest, and correcting the lesion estimation region according to a second user input to the lesion estimation region and thus labeling the lesion region on the region of interest.

Furthermore, the step of labeling the lesion region corresponding to the subject disease may further include the step of increasing a resolution for the region of interest, and the step of receiving the first user input may be performed after the step of increasing the resolution.

The step of labeling the lesion region corresponding to the subject disease may further include the step of returning the resolution of the region of interest on which the lesion region is labeled to an original resolution thereof.

The step of displaying the lesion estimation region may be performed by emphasizing the outer line of the lesion estimation region.

The labeling method may further include the step of storing the region of interest on which the lesion region is labeled.

According to another aspect of the present invention, a computing device for supporting labeling is provided. The computing device may include: at least one memory for storing a program for labeling, a communication unit for acquiring a medical image, and at least one processor for receiving the medical image, detecting regions of interest corresponding to at least one subject disease through a learned network function, and displaying the regions of interest on the medical image, and labeling a lesion region corresponding to the subject disease on the medical image according to the regions of interest and user inputs to the regions of interest.

Further, the processor may set the subject disease according to a user input.

Furthermore, the processor may correct at least one of the regions of interest according to a user input and crop and store the corrected region of interest from the medical image.

Also, the processor may receive a first user input for selecting a given region in the region of interest, set a reference pixel value for the selected given region, detect a region within the range of given pixel values from the reference pixel value as a lesion estimation region, display the detected lesion estimation region on the region of interest, correct the lesion estimation region according to a second user input to the lesion estimation region, and label the lesion region on the region of interest.

Moreover, the processor may increase a resolution for the region of interest and receive the first user input for selecting the given region in the region of interest whose resolution is increased.

Additionally, the processor may return the resolution of the region of interest on which the lesion region is labeled to an original resolution thereof.

Further, the processor may emphasizedly display the outer line of the lesion estimation region detected in the region of interest.

Moreover, the processor may store the region of interest on which the lesion region is labeled.

Advantageous Effects of the Invention

According to the present invention, the labeling method and the computing device therefor can detect the lesion estimation region corresponding to the subject disease through the learned network function, directly correct the lesion estimation region according to the user input, and more easily label the lesion region through the user.

The effectiveness of the labeling method and the computing device therefor according to the present invention is not limited as mentioned above, and it should be understood to those skilled in the art that the effectiveness of the disclosure may include another effectiveness as not mentioned above from the detailed description of the present invention.

BRIEF DESCRIPTION OF DRAWINGS

Now, a brief description of the drawings is given to allow the drawings suggested in the present invention to be more clearly understood.

MODE FOR DISCLOSURE

Figure 1:
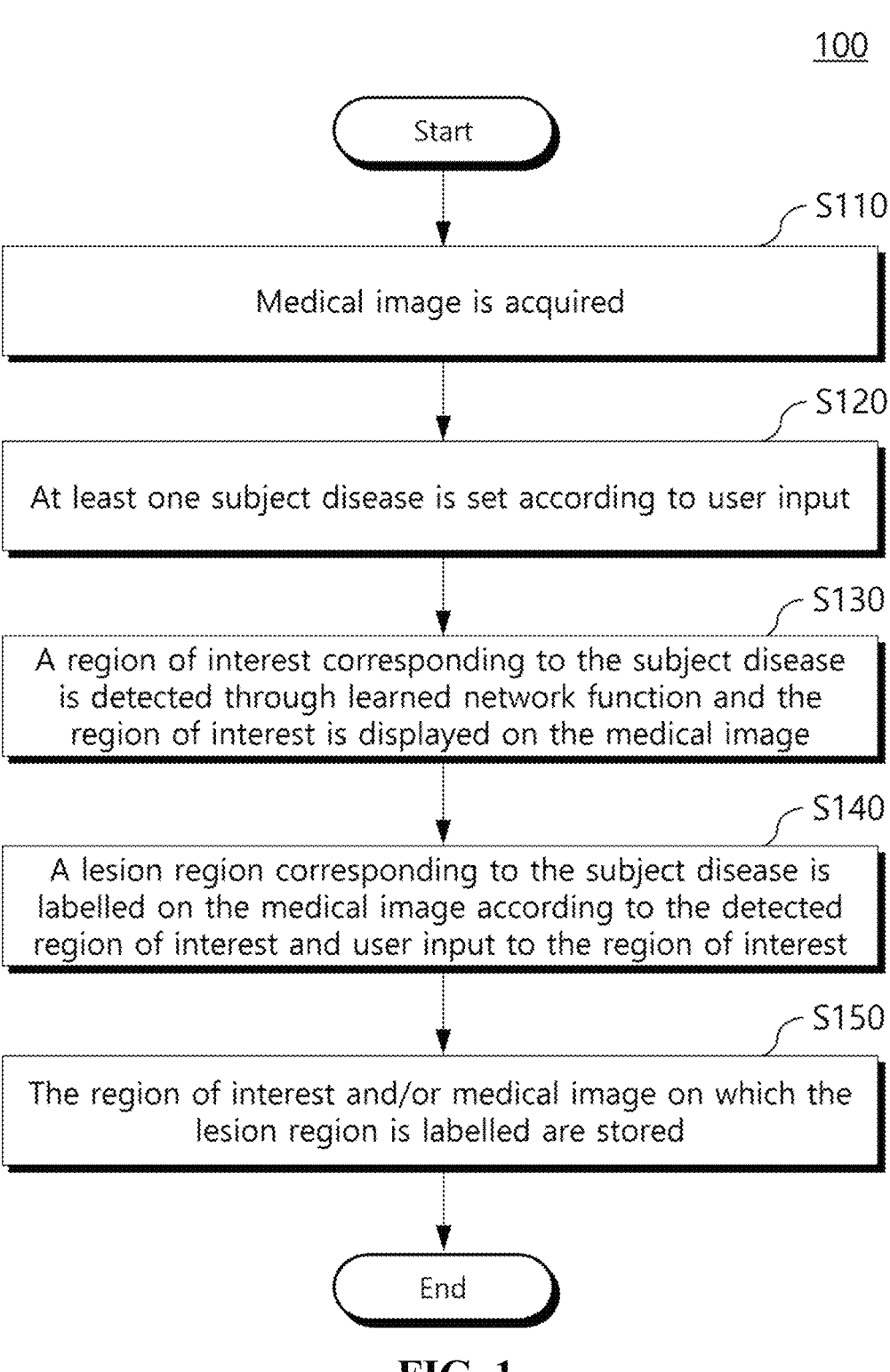
FIG. 1 is a flowchart showing a labeling method according to the present invention.

The present invention may be modified in various ways and may have several exemplary embodiments. Specific exemplary embodiments of the present invention are illustrated in the drawings and described in detail in the detailed description. However, this does not limit the disclosure within specific embodiments and it should be understood that the disclosure covers all the modifications, equivalents, and replacements within the idea and technical scope of the disclosure.

In the description, if it is determined that the detailed explanation on the well-known technology related to the present invention makes the scope of the present invention not clear, the explanation will be avoided for the brevity of the description. Terms, such as the first, the second, and the like, may be used to describe various elements, but the elements should not be restricted by the terms. The terms are used to only distinguish one element from the other element.

When it is said that one element is described as being "connected" or "coupled" to the other element, one element may be directly connected or coupled to the other element, but it should be understood that another element may be present between the two elements.

The terms "unit", "-or/er" and "module" described in the specification indicate a unit for processing at least one function or operation, which may be implemented by hardware, software or a combination thereof, such as a processor, a microprocessor, a microcontroller, a central processing unit (CPU), a graphics processing unit (GPU), an accelerate processor unit (APU), a digital signal processor (DSP), an application specific integrated circuit (ASIC), a field programmable gate array (FPGA), and the like.

Further, it should be appreciated that the division of the parts in the present invention is just made according to the principal functions the parts have. That is, two or more parts as will be discussed below, may be combined into one part, or one part may be divided into two or more parts according to more specified functions. Moreover, the respective parts as will be discussed in the specification, can additionally perform some or all of functions performed by other parts as well as their main functions, and of course, also, some of the main functions of the respective parts can be performed only by other parts.

Hereinafter, embodiments of the present invention will be described in detail sequentially.

In the description, a network function may be used with the same meaning as a neural network. In this case, the neural network is composed of interconnected calculation units, which are commonly called nodes, and the nodes are called neurons. Generally, the neural network is made up of a plurality of nodes. The nodes for constituting the neural network are connected to one another by means of one or more links.

In this case, some of the nodes constituting the neural network build one layer based on their distances from an initial input node. For example, a collection of nodes with the distances of n from the initial input node builds an n layer.

The neural network described in the present invention may include a deep neural network (DNN) having a plurality of hidden layers as well as input and output layers.

The network function includes a plurality of convolutional layers and a plurality of fully connected layers. The plurality of convolutional layers serve to perform the abstraction of the image to extract features, and the plurality of fully connected layers serve to predict the output probabilities of the detected objects.

FIG. 1 is a flowchart showing a labeling method according to the present invention.

A labeling method 100 according to an embodiment of the present invention may be performed by a personal computer, a work station, a server computer, and the like, which have operation ability, or by a separate device therefor.

Further, the labeling method 100 may be performed in one or more operation devices. For example, at least one or more steps of the labeling method 100 according to an embodiment of the present invention are performed in a client device, and other steps in a server device. In this case, the client device and the server device are connected to each other by a network and transmit and receive the results of operations to and from each other. Otherwise, the labeling method 100 according to the present invention may be performed through distributed computing.

At step S110, a medical image is acquired by a computing device. In this case, the medical image is a radiographic image, a computed tomography image, or the like for at least an area of a patient's body, but of course, the medical image may not be limited thereto.

For example, the computing device receives the patient's medical image from an external computing device connected thereto by means of wired and wireless communication, another device (e.g., medical imaging device) interworking therewith, or an external storage medium.

At step S120, at least one subject disease is set by the computing device according to user inputs. In this case, the subject disease is an object on which labeling is performed by the user, so that a lesion region is labeled on the medical image.

For example, the computing device provides a given user interface for the selection of the subject disease, and through the user interface, at least one of a plurality of diseases is selected as the subject disease by the user.

After the medical image has been received, at step S130, the computing device detects a region of interest corresponding to the at least one subject disease through a learned network function and displays the region of interest on the medical image. In this case, the region of interest represents a region on which features or specific anatomical features the lesion region of a specific disease has are included.

The network function has pre-learning for detection of the region of interest and/or lesion region through learning data (for example, medial images on which the regions of interest or lesion regions are detected by a specialist or other network functions).

In the embodiment of the present invention, the network function detects the region of interest from the medical image to the form of a boundary box and displays the detected region of interest on the medical image.

At step S140, the computing device labels the lesion region corresponding to the subject disease on the medical image according to the detected region of interest and the user inputs to the region of interest.

For example, the computing device corrects the outer boundary line of the region of interest or limits a given region within the region of interest to the lesion region according to user inputs, thereby completing the labeling of the lesion region corresponding to the subject disease on the medical image.

The step S140 will be explained in more detail later with reference to FIGS. 2 and 3.

At step S150, the labeled region of interest and/or medical image are stored in a memory of the computing device or in a database server connected to the computing device through communication.

In the embodiment of the present invention, the computing device crops and sortedly stores the region of interest on which the lesion region is labeled from the medical image or stores the entire medical image on which the lesion region is labeled, according to user inputs. In the embodiment of the present invention, while the region of interest and/or the medical image are being stored, image equalization, brightness adjustment, size control, blur application, sharpening application, conversion of black-and-white image to color image, RGB value designation, and the like may be performed by the computing device according to user inputs.

The stored region of interest and/or medical image may be used as learning data for a second network function adapted to read lesions of the subject disease.

Figure 2:
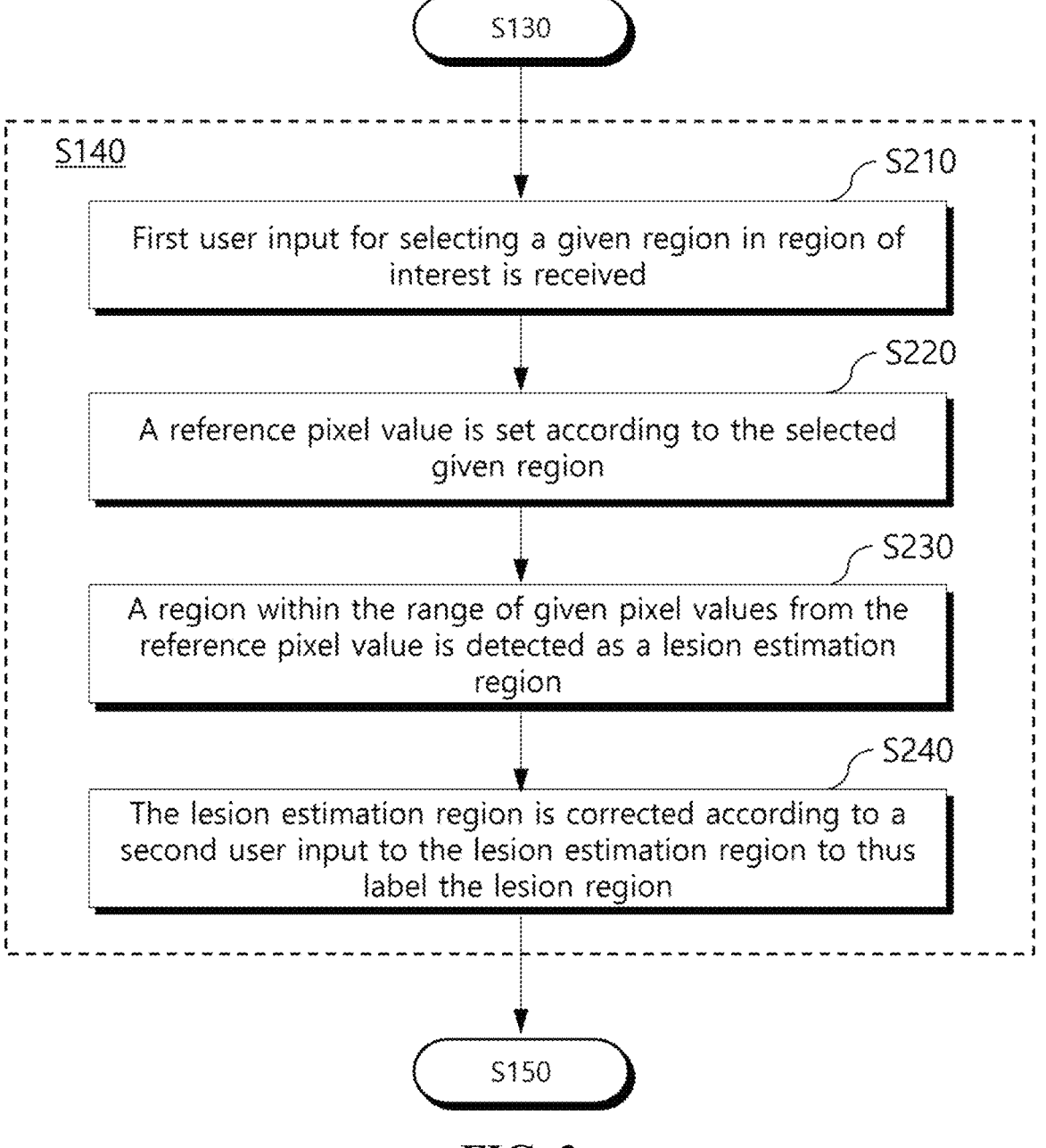
FIG. 2 is a flowchart showing an embodiment of step S140 of FIG. 1.

FIG. 2 is a flowchart showing an embodiment of step S140 of FIG. 1.

Referring to FIG. 2, the step S140 of FIG. 1 includes steps S210 to S240.

At step S210, the computing device receives a first user input for selecting a given region in the region of interest.

For example, the first user input is an input for the selection of the given region in the region of interest through a mouse cursor. In specific, the user checks the region of interest displayed on the medical image and directly selects the given region within the region of interest determined as the lesion region through the mouse curser.

At step S220, the computing device sets a reference pixel value for the given region selected at the step S210. In this case, the pixel value represents the discrete value for color, brightness, or other properties a given pixel has. In specific, the R, G, and B color values of the given pixel are set with integer values within a given range (e.g., 0 to 360), and the brightness value of the given pixel is set with an integer value within a given range (e.g., 0 to 100).

At the step S220, accordingly, the color value or brightness value of the given region selected by the user input is set as the reference pixel value by the computing device.

At step S230, a region within the range of given pixel values from the reference pixel value with respect to the given region selected by the user input is detected as a lesion estimation region by the computing device, and next, the lesion estimation region is displayed on the region of interest and/or the medical image by the computing device.

The region corresponding to the lesion on the medical image may have similar properties of colors and brightness to other regions, and accordingly, the reference pixel value is set at a point determined as the lesion region by the user. Next, if the region within the range of given pixel values from the corresponding point is detected, it is likely that the detected region corresponds to the lesion region. Accordingly, the detected region is detected as the lesion estimation region and displayed on the region of interest and/or the medical image by the computing device.

For example, if the reference pixel value is set to 100, the region with pixel values in the range of +/−2 from the reference pixel value 100, that is, the region with the pixel values 98 to 102 is detected as the lesion estimation region.

In the embodiment of the present invention, the outer line of the lesion estimation region is displayed emphasizedly with a given color or thickness.

In the embodiment of the present invention, a plurality of lesion estimation regions are detectable by the computing device. In specific, the pixel value regions within different ranges with respect to the reference pixel value are detected as the lesion estimation regions. For example, if the reference pixel value is set to 100, the region with the pixel values in the range of +/−2 from the reference pixel value 100, that is, the region with the pixel values 98 to 102 is detected as a first lesion estimation region, and the region with the pixel values in the range of +/−4 from the reference pixel value 100, that is, the region with the pixel values 96 to 104 is detected as a second lesion estimation region. The detected lesion estimation regions are emphasized on their outer line and then displayed on the region of interest and/or the medical image. Accordingly, the outer lines of the plurality of lesion estimation regions are displayed on the region of interest and/or the medical image to the form of contour lines.

At step S240, the lesion estimation region is corrected by the computing device according to a second user input to the lesion estimation region to thus label the lesion region on the region of interest and/or the medical image.

For example, if a portion of the outer line of the lesion estimation region is dragged by the user through the mouse cursor, the portion is moved, enlarged, reduced, or deformed by the computing device so that the lesion estimation region is corrected to label the lesion region on the region of interest and/or the medical image. The labeling information of the lesion region includes the information of a disease, a progression degree, and the like corresponding to the lesion region.

Figure 3:
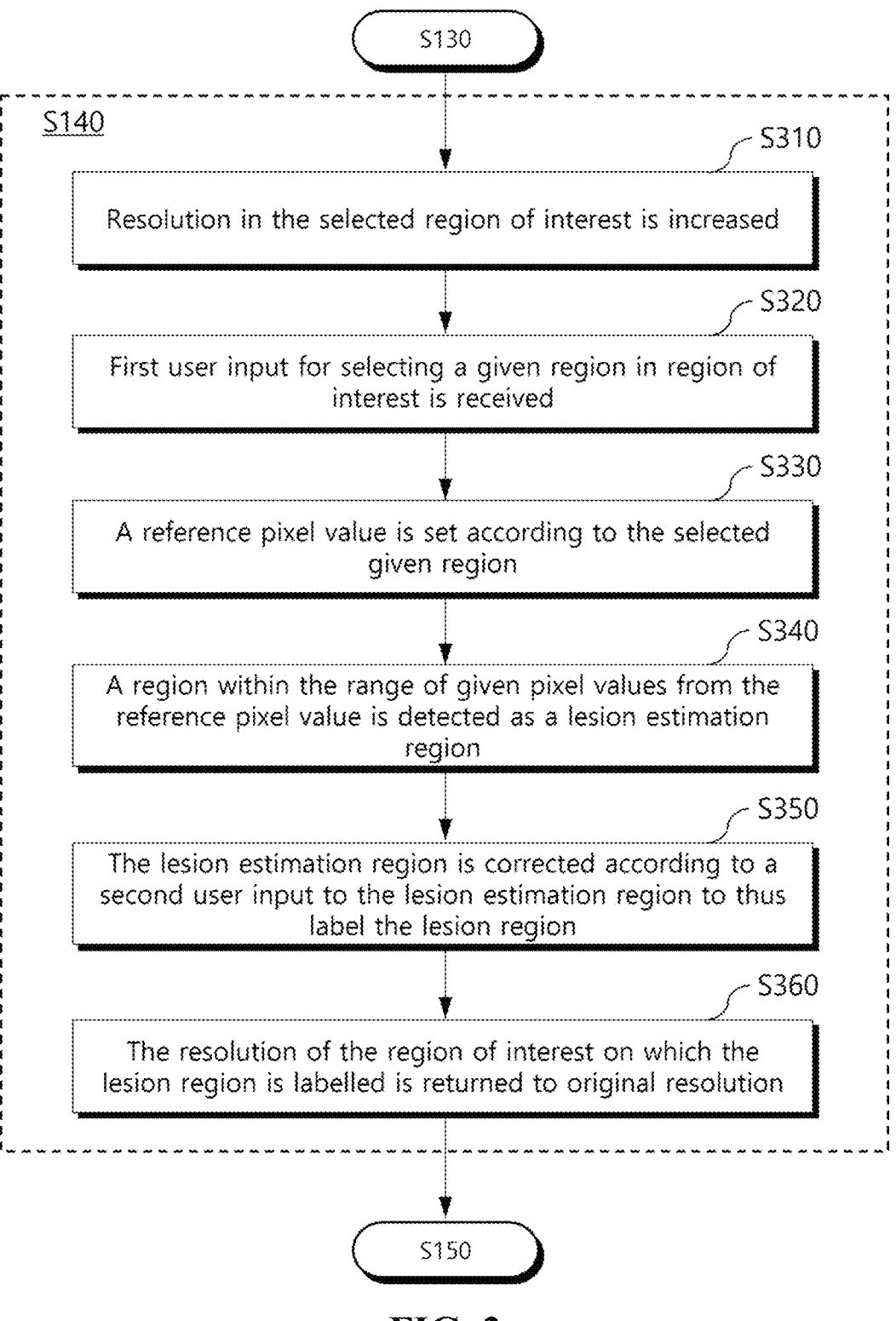
FIG. 3 is a flowchart showing another embodiment of step S140 of FIG. 1.

FIG. 3 is a flowchart showing another embodiment of step S140 of FIG. 1.

Referring to FIG. 3, the step S140 of FIG. 1 includes steps S310 to S360. The steps S320 to S350 of FIG. 3 are the same as the steps S210 to S240 of FIG. 2, and for the brevity of the description, differences between the two embodiments will be explained.

At step S310, a resolution for at least one of detected regions of interest is increased by the computing device. For example, if one of the regions of interest displayed on the medical image is selected by the user, the resolution for the selected region is increased by the application of a subpixel method.

Next, the steps S320 to S350 are performed for the region of interest whose resolution is increased. Accordingly, the user performs the labeling for the lesion region more accurately and easily.

If the labeling for the region of interest whose resolution is increased is completed, at step S360, the resolution of the region of interest is returned to its original resolution equal to the resolution of the medical image.

After that, as mentioned above, the medical image on which the lesion region is labeled is stored in the memory or the external database server and used as the learning data for the second network function adapted to read the lesion of the subject disease.

Figure 4:
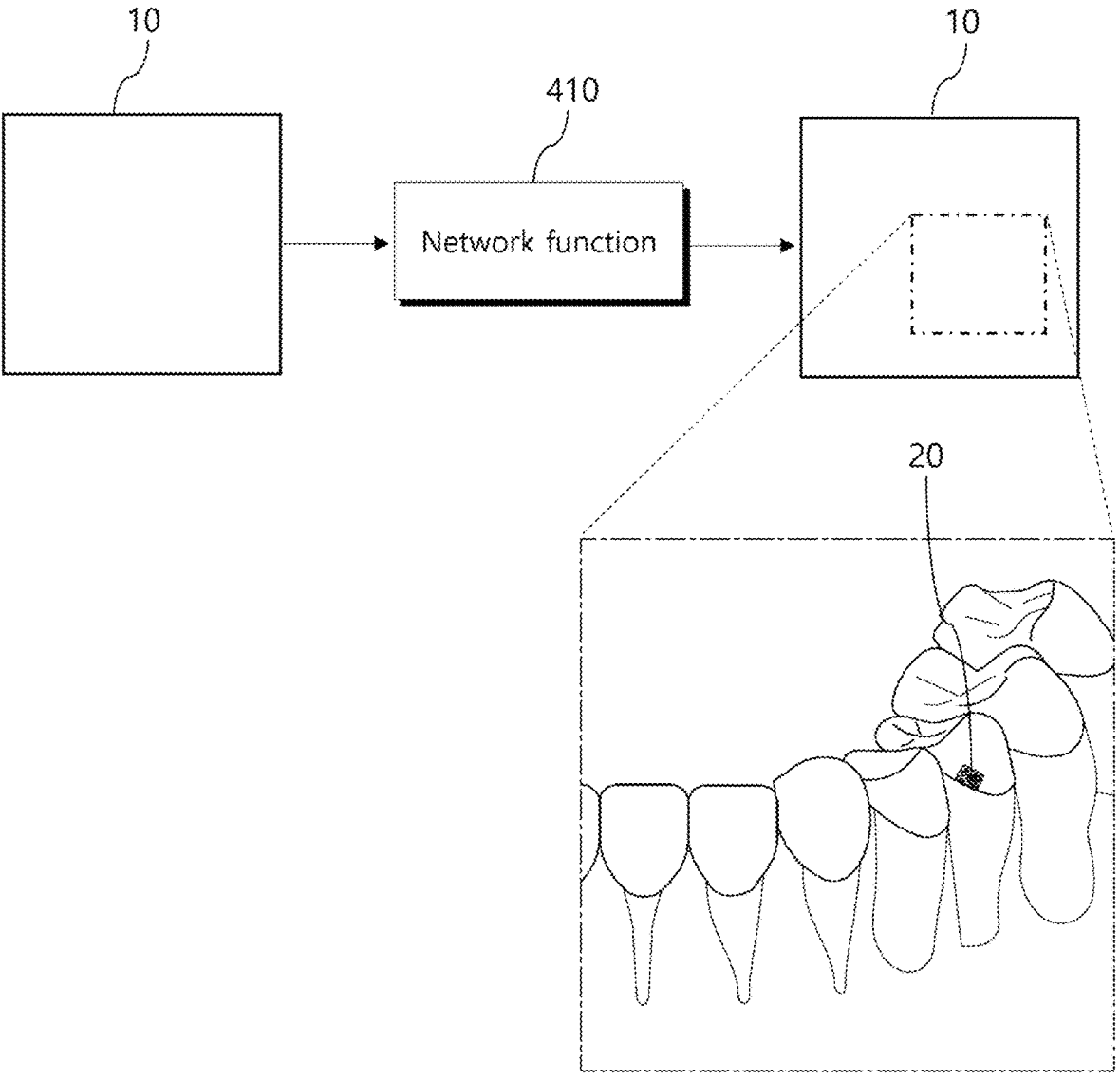
FIGS. 4 and 5 are exemplary views showing an example of operations of network functions in the labeling method according to the present invention.
Figure 5:
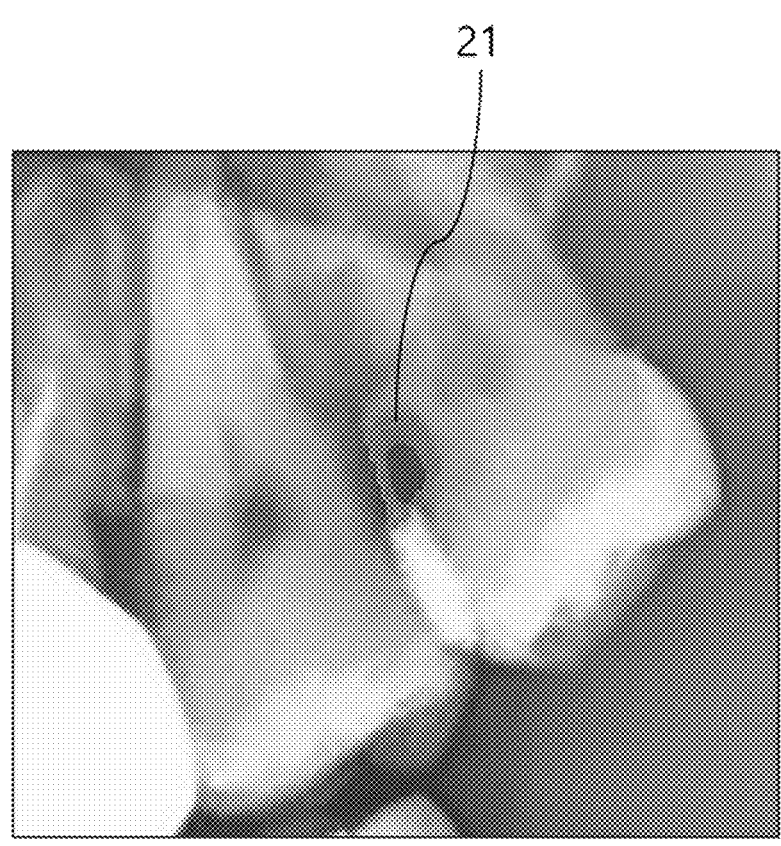

FIGS. 4 and 5 are exemplary views showing an example of operations of network functions in the labeling method according to the present invention.

Referring to FIGS. 4 and 5, the medical image 10 inputted to the network function 410 is a dental image with the teeth of a patient, and the subject disease is a dental disease such as dental caries, and the like. Further, the dental image is a cephalometric radiographic image, a panoramic radiographic image, or the like, but it may not be limited thereto.

As mentioned above, the network function 410 has prelearning for the detection of the region of interest 20, 21 and/or the lesion region through learning data (e.g., the medical images from which the region of interest 20, 21 and/or the lesion region are detected by the specialist or other network functions). Further, the network function 410 is used to pre-display the region of interest 20, 21 or the lesion estimation region to assist the labeling, and accordingly, the neural network that places more emphasis on a detection speed than accuracy the network function used for real lesion reading has may be adopted as the network function 410.

If the medical image 10 is inputted to the network function 410 by the computing device, the network function 410 detects the region of interest 20, 21 in which the lesion region such as dental caries is included from the medical image 10, and the detected region of interest 20, 21 is displayed on the medical image 10 by the computing device. In this case, the region of interest 20, 21 is the same as the lesion estimation region, and the detected region of interest is corrected through given methods by the user, thereby performing the labeling of the lesion region on the medical image 10.

Figure 6:
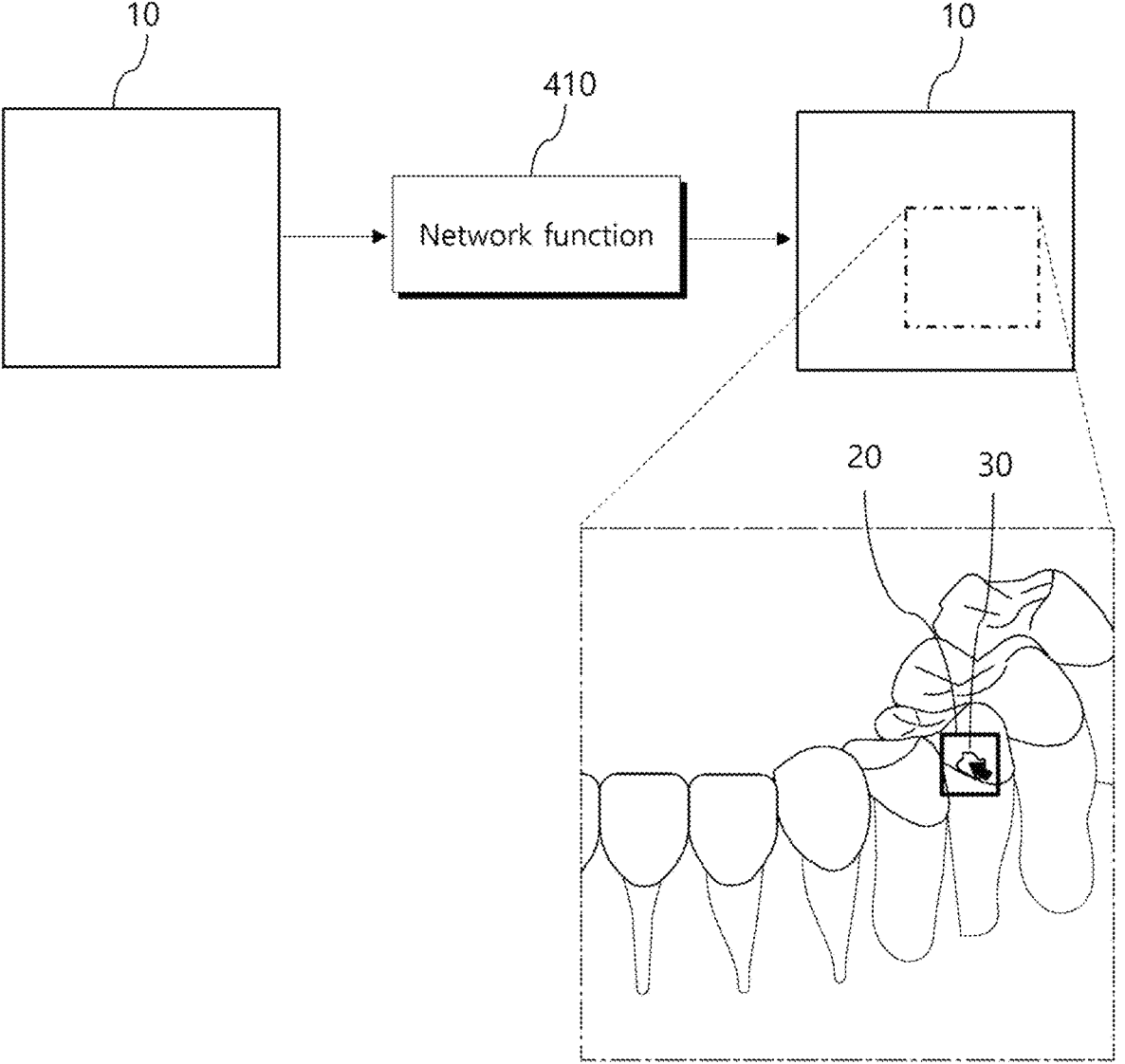
FIGS. 6 and 7 are exemplary views showing another example of operations of network functions in the labeling method according to the present invention.
Figure 7:
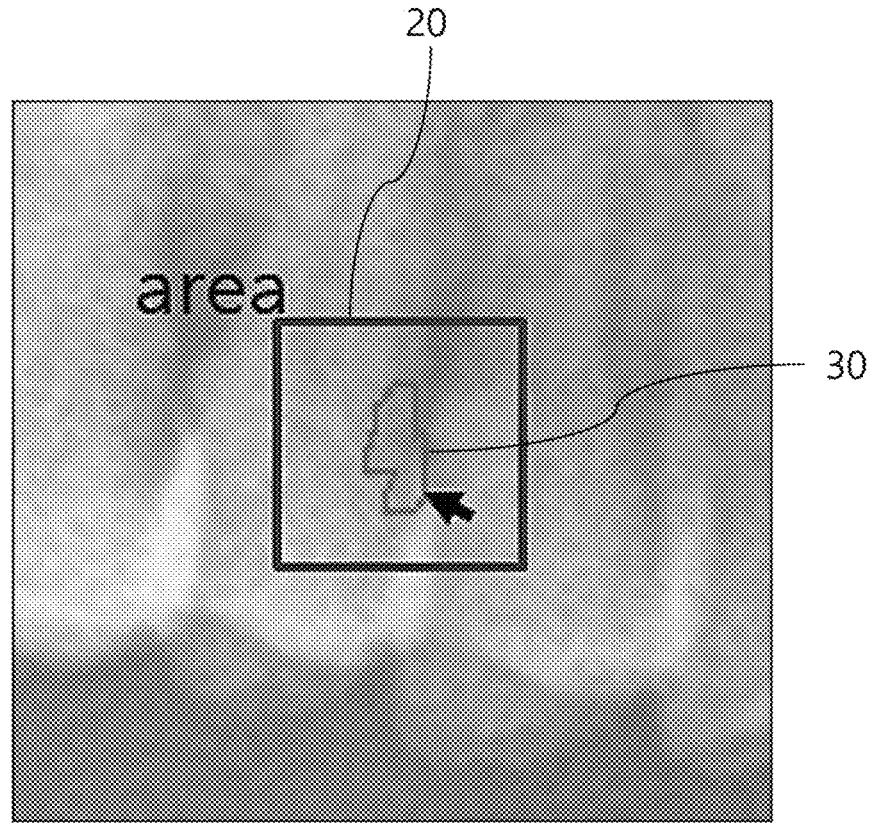

FIGS. 6 and 7 are exemplary views showing another example of operations of network functions in the labeling method according to the present invention.

Referring to FIGS. 6 and 7, the computing device additionally detects the lesion estimation region 30 according to the first user input to the detected region of interest through the network function, and the detected lesion estimation region is corrected according to the second user input, thereby performing the labeling of the lesion region.

As shown in FIGS. 6 and 7, for example, if the computing device detects the region of interest 20 to a square box shape through the network function and displays the detected region of interest 20 on the medical image, the region of interest 20 is read directly by the user, and next, a given point (or region) determined as a lesion is selected through the mouse cursor.

Next, the computing device sets the reference pixel value according to the pixel value of the given point selected by the user, and the region having pixel values in a given range of the selected point of the user from the reference pixel value is detected as the lesion estimation region 30. In this case, the outer line of the detected lesion estimation region 30 is displayed emphasizedly with a given color or thickness.

Next, if the outer line of the lesion estimation region 30 is dragged by the user through the mouse cursor, the outer line is corrected by the computing device so that the corrected lesion estimation region 30 is labeled on the region of interest 20 and/or the medical image 10.

Figure 8:
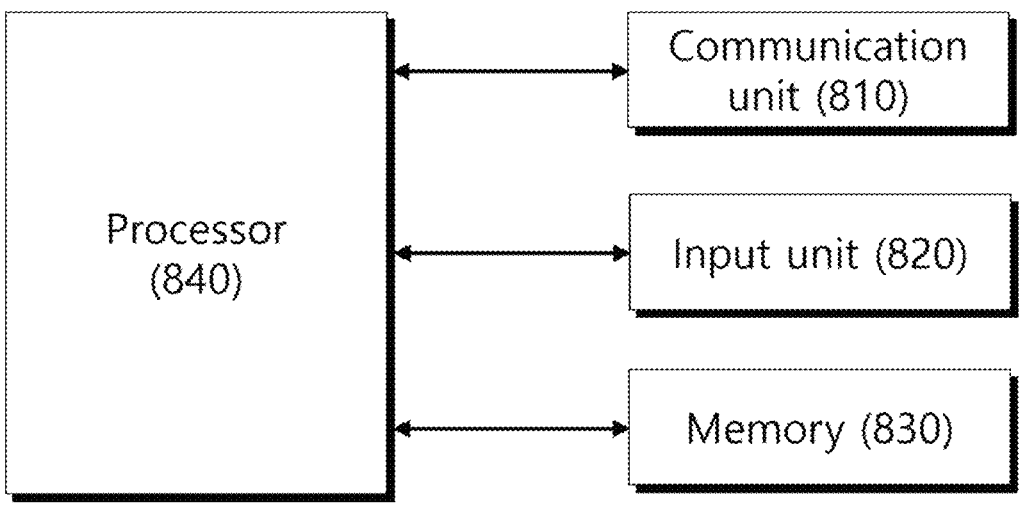
FIG. 8 is a schematic block diagram showing a computing device for performing the labeling method according to the present invention.

FIG. 8 is a schematic block diagram showing the computing device for performing the labeling method according to the present invention.

A communication unit 810 receives input data (medical image, etc.) for labeling. The communication unit 810 includes wired and wireless communication units. If the communication unit 810 includes the wired communication unit, the communication unit 810 includes one or more components for performing communication with a local region network (LAN), a wide region network (WAN), a value added network (VAN), a mobile radio communication network, a satellite communication network, and a combination thereof. Further, if the communication unit 810 includes the wireless communication unit, the communication unit 810 transmits and receives data or signals wirelessly by using cellular communication, wireless LAN (e.g., Wi-Fi), and the like. According to the present invention, the communication unit 810 transmits and receives data or signals to and from an external device or external server under the control of a processor 840 as will be discussed later.

An input unit 820 receives various user commands through external control. To do this, the input unit 820 includes one or more input devices or is connected to the input devices. For example, the input unit 820 is connected to an interface for various inputs such as a keypad, a mouse, and the like and receives the user commands from the interface. To do this, the input unit 820 includes an interface such as a USB port, a Thunderbolt interface, and the like. Further, the input unit 820 includes various input devices such as a touch screen, a button, and the like or is connected to the input devices to receive the user commands from the outside.

A memory 830 stores programs and/or program commands for operating the processor 840 and temporarily or permanently stores data inputted and outputted. The memory 830 includes at least one storage medium of a flash memory, a hard disc, a multimedia card micro storage medium, a card type memory (e.g., SD or XD memory), random access memory (RAM), a static RAM (SRAM), a read-only memory (ROM), an electrically erasable programmable ROM (EEPROM), a programmable ROM (PROM), a magnetic memory, a magnetic disc, and an optical disc.

Further, the memory 830 stores various network functions and algorithms, while storing various data, programs (with one or more instructions), applications, software, commands, and codes for operating and controlling the computing device 800 according to the present invention.

The processor 840 controls all of the operations of the computing device 800. The processor 840 executes one or more programs stored in the memory 830. The processor 840 represents a central processing unit (CPU), a graphics processing unit (GPU), or a dedicated processor through which the method, according to the technical ideas of the present invention, is performed.

According to the embodiment of the present invention, the processor 840 acquires a medical image, receives the medical image, detects regions of interest corresponding to at least one subject disease through a learned network function, displays the regions of interest on the medical image, and labels a lesion region corresponding to the subject disease on the medical image according to the regions of interest and user inputs to the regions of interest.

The labeling method, according to the embodiments of the present invention, may be implemented in the form of a program instruction that can be performed through various computing means, and the labeling method may be recorded in a computer readable recording medium. The computer-readable medium may include a program command, a data file, a data structure, and the like, independently or in combination. The program instruction recorded in the recording medium is specially designed and constructed for the present invention, but it may be well known to and may be used by those skilled in the art of computer software. The computer-readable recording medium may include a magnetic medium such as a hard disc, a floppy disc, and a magnetic tape, an optical recording medium such as a compact disc read-only memory (CD-ROM) and a digital versatile disc (DVD), a magneto-optical medium such as a floptical disk, and a hardware device specifically configured to store and execute program instructions, such as a read-only memory (ROM), a random access memory (RAM), and a flash memory. Further, the program command may include a machine language code generated by a compiler and a high-level language code executable by a computer through an interpreter and the like.

Further, the labeling method, according to the disclosed embodiments of the present invention, is included in a computer program product. The computer program product as a product may be traded between a seller and a buyer.

The computer program product may include an S/W program and a computer-readable storage medium in which the S/W program is stored. For example, the computer program product may include an S/W program type product (e.g., downloadable app) electronically distributed through a manufacturing company of an electronic device or electronic market (e.g., Google play store, an app store, etc.). To do such electronic distribution, at least a portion of the S/W program may be stored in the storage medium or temporarily produced. In this case, the storage medium may be a storage medium of a server of the manufacturing company, a server of the electronic market, or a broadcast server for temporarily storing the S/W program.

The computer program product may include a storage medium of a server or a storage medium of a client device in a system composed of the server and the client device. If a third device (e.g., smartphone) connected to the server or client device exists, the computer program product may include a storage medium of the third device. Otherwise, the computer program product may include an S/W program itself transmitted from the server to the client device or the third device or from the third device to the client device.

In this case, one of the server, the client device, and the third device executes the computer program product to perform the method according to the embodiments of the present invention. Further, two or more devices of the server, the client device and the third device execute the computer program product to distributedly perform the method according to the embodiments of the present invention.

For example, the server (e.g., a cloud server or artificial intelligence server) executes the computer program product stored therein and controls the client device connected thereto to perform the method according to the embodiments of the present invention.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

The invention claimed is:

1. A labeling method comprising:
obtaining a medical image;
receiving the medical image, detecting a region of interest corresponding to at least one subject disease using a learned network function, and displaying the region of interest on the medical image; and
labeling a lesion region on the medical image corresponding to the at least one subject disease, based on the region of interest and user inputs to the region of interest,
wherein the labeling the lesion region comprises:
receiving a first user input for choosing a selected region within the region of interest,
setting a reference pixel value based on the selected region,
detecting, as at least one lesion estimation region, at least one region having pixel values within a predetermined pixel value range from the reference pixel value and displaying the at least one lesion estimation region on the region of interest, and
correcting the at least one lesion estimation region according to a second user input to the at least one lesion estimation region and labeling the at least one corrected lesion estimation region as the lesion region on the region of interest,
wherein the reference pixel value represents a color value or a brightness value of the selected region, and
wherein the pixel values of the at least one region detected as the at least one lesion estimation region represent the color value or the brightness value within the predetermined pixel value range from the reference pixel value.

2. The labeling method according to claim 1, further comprising: setting the at least one subject disease according to the user inputs.

3. The labeling method according to claim 1, further comprising: correcting at least one of the regions of interest according to the user inputs and cropping and storing a corrected region of interest from the medical image.

4. The labeling method according to claim 1, wherein the labeling the lesion region further comprises: increasing a resolution of the region of interest, and the receiving the first user input is performed after the increasing the resolution.

5. The labeling method according to claim 4, wherein the labeling the lesion region further comprises: returning the resolution of the region of interest on which the lesion region is labeled to an initial resolution thereof.

6. The labeling method according to claim 1, wherein the displaying the at least one lesion estimation region is performed by emphasizing an outer line of the at least one lesion estimation region.

7. The labeling method according to claim 1, further comprising: storing the region of interest on which the lesion region is labeled.

8. The labeling method according to claim 1, wherein the at least one lesion estimation region includes a plurality of lesion estimation regions.

9. The labeling method according to claim 8,
wherein the plurality of lesion estimation regions include a first lesion estimation region and a second lesion estimation region, wherein the first lesion estimation region has the pixel values within a first predetermined pixel value range from the reference pixel value, and wherein the second lesion estimation region has the pixel values within a second predetermined pixel value range from the reference pixel value.

10. A computing device for supporting labeling, the computing device comprising:

at least one memory for storing a computer program for labeling;

a wired or wireless communication interface configured to obtain a medical image; and at least one processor receiving the medical image, detecting a region of interest corresponding to at least one subject disease using a learned network function, and displaying the region of interest on the medical image, and labeling a lesion region on the medical image corresponding to the at least one subject disease, based on the region of interest and user inputs to the regions of interest, wherein the at least one processor receives a first user input for choosing a selected region within the region of interest, sets a reference pixel value based on the selected region, detects, as at least one lesion estimation region, at least one region having pixel values within a predetermined pixel value range from the reference pixel value and displays the at least one lesion estimation region on the region of interest, corrects the at least one lesion estimation region according to a second user input to the at least one lesion estimation region, and labels the at least one corrected lesion estimation region as the lesion region on the region of interest, wherein the reference pixel value represents a color value or a brightness value of the selected region, and wherein the pixel values of the at least one region detected as the at least one lesion estimation region represent the color value or the brightness value within the predetermined pixel value range from the reference pixel value.

11. The computing device according to claim 10, wherein the at least one processor sets the at least one subject disease according to the user inputs.

12. The computing device according to claim 10, wherein the at least one processor corrects at least one of the regions of interest according to the user inputs and crops and stores a corrected region of interest from the medical image.

13. The computing device according to claim 10, wherein the at least one processor increases a resolution for the region of interest and receives the first user input for choosing the selected region in the region of interest whose resolution is increased.

14. The computing device according to claim 13, wherein the at least one processor returns the resolution of the region of interest on which the lesion region is labeled to an initial resolution thereof.

15. The computing device according to claim 10, wherein the at least one processor displays an outer line of the at least one lesion estimation region detected in the region of interest.

16. The computing device according to claim 10, wherein the at least one processor stores the region of interest on which the lesion region is labeled.

17. The computing device according to claim 10, wherein the at least one lesion estimation region includes a plurality of lesion estimation regions.

18. The computing device according to claim 17, wherein the plurality of lesion estimation regions include a first lesion estimation region and a second lesion estimation region, wherein the first lesion estimation region has the pixel values within a first predetermined pixel value range from the reference pixel value, and wherein the second lesion estimation region has the pixel values within a second predetermined pixel value range from the reference pixel value.

* * * * *